United States Patent [19]

Gibbons et al.

[11] 4,287,300

[45] Sep. 1, 1981

[54] CHARGE EFFECTS IN ENZYME IMMUNOASSAYS

[75] Inventors: Ian Gibbons, Menlo Park; Gerald L. Rowley, Cupertino; Edwin F. Ullman, Atherton, all of Calif.

[73] Assignee: Syva Company, Palo Alto, Calif.

[21] Appl. No.: 61,099

[22] Filed: Jul. 26, 1979

[51] Int. Cl.$^3$ .................. C12Q 1/70; G01N 33/54; C12N 9/96

[52] U.S. Cl. .................................. 435/5; 435/7; 435/188; 435/810; 424/12; 23/230 B

[58] Field of Search ............... 435/4, 7, 177, 188, 435/805, 810, 5; 424/8, 12, 85; 260/112, 121; 252/408 R; 73/230 B; 422/8

[56] References Cited

U.S. PATENT DOCUMENTS

| | | | |
|---|---|---|---|
| 3,817,837 | 6/1974 | Rubenstein et al. | 435/7 |
| 3,996,345 | 12/1976 | Ullman et al. | 435/7 |
| 4,104,029 | 8/1978 | Maier et al. | 435/188 |
| 4,193,983 | 3/1980 | Ullman et al. | 435/7 |
| 4,203,802 | 5/1980 | Rubenstein et al. | 435/7 |

OTHER PUBLICATIONS

Wallenfels et al., *The Enzymes*, vol. 3, (Boyer ed.), Academic Press, N.Y. (1972) pp. 617-663.
Rowley, et al. "Mechanism by which Antibodies Inhibit Hapten-Malate Dehydrogenase Conjugates", *J. Biol. Chem.* vol. 250 No. 10, (1975), pp. 3759-3766.
Engasser, et al., "Diffusion and Kinetics with Immobilized Enzymes", *Applied Biochemistry and Bioengineering*, vol. 1, (Wingard et al. ed.), Academic Press, N.Y. (1976) pp. 127-145, 194-205.
Rubenstein, et al., "Homogeneous' Enzyme Immunoassay, a New Immunochemical Technique", *Biochem. Biophys. Res. Comm.*, vol. 47, No. 4 (1972) pp. 846-851.
Nargessi et al., "Use of Antibodies Against the Label in Non-Separation Non-Iostopic Immunoassay: Indirect Quenching Fluorimmunoassay of Proteins"*J. Immunol. Meth.*, vol. 26, No. 4, (1979) pp. 307-313.
Gibbons et al., "Homogeneous Enzyme Immunoassay for Proteins Employing B-Galactosidase", *Anal. Biochem.*, vol. 102 No. 1 (1980) pp. 167-170.
"Enzyme Immunoassays Revisited", *The Lancet*, vol. 11, (1979), pp. 780-781.
Schuurs et al., "Enzyme-Immunoassay", *Chin. Chim. Acta*, vol. 81, No. 1, (1977) pp. 1-40.

*Primary Examiner*—Thomas G. Wiseman
*Attorney, Agent, or Firm*—Bertram I. Rowland

[57] ABSTRACT

A method for determining a member of a specific binding pair-ligand and receptor (antiligand). Reagents employed include a first modified member which provides an electrical field due to the presence of a plurality of ionic charges and a second modified member labeled with a component of a signal producing system, which system may have one or more components. The average proximity in the assay medium of the first and second modified members is related to the amount of analyte, where the observed signal from the signal producing system is related to the effect of the electrical field on the signal producing system.

Also, compositions are provided, as well as reagents, in predetermined ratios for optimizing the signal response to variations in analyte concentration.

15 Claims, No Drawings

CHARGE EFFECTS IN ENZYME IMMUNOASSAYS

BACKGROUND OF THE INVENTION

1. Field of the Invention

Protein binding assays or immunoassays have been the subject of thorough investigation and commercialization. The ability to specifically determine a drug or other compound of interest, particularly physiological interest, which is present in extremely low concentration, usually less than micrograms per milliliter, has opened up new opportunities in clinical laboratories. The ability to monitor therapeutic drug administration or drug addiction, to rapidly and efficiently determine diseased states, and to monitor the condition of a patient during times of stress, has provided significant opportunities for improvement of health care.

The assays in the clinical laboratory frequently require not only high sensitivity but accuracy over a relatively narrow range. Therefore, new techniques are being developed which recognize these requirements by providing for greater sensitivity, reduced response to non-specific effects, and easier and simpler protocols. In addition, many antigens can be obtained only in impure form or in pure form at elevated costs. Therefore, assays must accomodate the possibility that the antigen will be impure. Parallel to this situation is that most antibodies which are obtained by antigenic injection will have less than about 30 weight %, or frequently less than about 20 weight % of the total protein as the antibody of interest. When preparing reagents which involve reactions with the antibody composition, the presence of the large amount of contaminant must be taken into account.

Other considerations in developing an assay include the necessity for and number of incubations, the period required for the incubation, the period required for the measurement, the sensitivity of the measurement to extraneous factors, the stability of the reagents, the formulation of the reagents, and the like.

2. Description of the Prior Art

U.S. Pat. No. 3,996,345 describes the employment of a chromophore pair—fluorescer and quencher—, where the members of the pair are bonded to different members of a specific binding pair, so that the amount of fluorescer and quencher which come within an interacting distance is dependent upon the amount of analyte in the medium. U.S. Pat. No. 3,935,074 describes an immunoassay dependent upon the inability of two antibodies to simultaneously bind to a reagent having at least two determinant sites. Co-pending application Ser. No. 893,650, filed Apr. 5, 1978, U.S. Pat. No. 4,233,402, teaches the concept in immunoassays of bringing together two enzymes, whose substrates or products are in some ways related to the production of a detectible signal, where the juxtaposition of the enzymes is related to the amount of analyte in the medium. Co-pending application Ser. No. 815,632, filed July 14, 1977, U.S. Pat. No. 4,208,479, teaches the employment of a macromolecular modifier of a label bound to an antibody, where the modifier is inhibited from approaching the label when the labeled antibody is bound to antigen. Co-pending application Ser. No. 815,487, filed July 14, 1977, U.S. Pat. No. 4,233,401, discloses an enzyme immunoassay where ligand is labeled with enzyme and an enzyme inhibitor is inhibited from approaching the enzyme, when antibody is bound to the ligand. Co-pending application Ser. No. 964,099, filed Nov. 24, 1978, discloses the use of macromolecular particles to provide discrimination between a label bound to the particle and a label free in the solution, where the amount of label bound to the particle is related to the amount of analyte in the medium, and the observed detectible signal is dependent upon the distribution of the label between the particle and the medium. U.S. Pat. No. 3,817,837 describes a homogeneous enzyme immunoassay.

SUMMARY OF THE INVENTION

A protein binding assay is provided involving members of a specific binding pair, the members being ligand and receptor (antiligand). As a first reagent in the method, one of the members is substituted with a plurality of ionizable functionalities which are capable of providing a charge, either positive or negative, under the assay conditions. A second member, either the same or homologous member, is labeled with a component of a signal producing system, which signal producing system is able to produce a detectible signal under the assay conditions.

The signal produced by the signal producing system is affected by the juxtaposition of the electrical field resulting from the charged first member. By appropriate choice of the members in relation to the analyte, the average proximity of the first and second members in the assay medium can be related to the amount of analyte in the assay medium. Thus, the observed signal can be related to the amount of analyte in the assay medium. By employing appropriate standards having known amounts of analyte, one can establish a relationship between concentration of the analyte and the level of observed signal.

In addition, reagents are provided for the assay, as well as combinations of reagents which provide for substantial optimization of the sensitivity of the assay or level of response of the assay to variations in the concentration of the analyte.

DESCRIPTION OF THE SPECIFIC EMBODIMENTS

The subject invention is concerned with a protein binding assay, involving a specific binding pair, ligand and receptor. The basis of the invention is to relate the proximity of two reagents to the amount of analyte in the assay medium. The first reagent, is a first member of the specific binding pair which is modified with a plurality of ionic charges, so as to create a charged field in an aqueous environment at a predetermined pH. A second member is modified with a label, which is one component of a single or multicomponent signal producing system; the level of the observed signal is dependent upon the juxtaposition of the signal producing system to the field created by the charged member. The field affects the signal producing system by enhancing or diminishing the localized concentration of certain ions in the assay medium, which ionic concentration affects the level of the observed signal. In addition to the analyte and the first and second members, other materials may also be added depending upon the nature of the signal producing system.

The binding of homologous members of the specific binding pair results in the formation of a complex, where two or more, usually three or more members are involved. In view of the polyvalent nature of antibodies and antigens, the complex can be extended to create a network of antibody and antigen bringing a plurality of signal labels and ionic charges into proximity, where interactions can occur.

In discussing the subject invention, the following order will be involved. First, the assay method will be considered. This will be followed by definitions defining various terms in relation to the materials employed. Following the definitions, the materials will be discussed as to the analyte, signal producing system, and charged member. This will be followed by the experimental and demonstration of the utility of the subject method.

ASSAY METHOD

In accordance with the subject method, the analyte, a reagent having a plurality of ionizable groups which are substantially ionized under the conditions of the assay, a labeled reagent, where the label is a member of a signal producing system and any necessary additional components are combined in a buffered aqueous medium. The observed signal may then be read and compared to an assay medium having a known amount of analyte.

The analyte is a member of a specific binding pair, consisting of ligand and its homologous receptor, and either the ligand or the receptor may be the analyte. The assay medium is normally aqueous, which is normally buffered in sufficient amount to a moderate pH, generally close to providing optimum assay sensitivity. The assay is performed without separation of the assay components or products.

The aqueous medium may be solely water, or may include from zero to 40 volume percent of a cosolvent, normally a polar solvent, usually an oxygenated organic solvent or from one to six, more usually of from one to four carbon atoms, including alcohols, ethers, and the like.

The pH for the medium will usually be in the range of about 4 to 11, more usually in the range of about 5 to 10, and preferably in the range of about 6.5 to 9.5. The pH is chosen so as to maintain a significant level of specific binding by the receptor, while optimizing the sensitivity or response of the signal producing system to variations in analyte concentration.

Various buffers may be used to achieve the desired pH and maintain the pH during the determination. Illustrative buffers include borate, phosphate, carbonate, tris, barbital and the like. The particular buffer employed is not critical to this invention, but in individual assays, one or another buffer may be preferred.

Moderate temperatures are normally employed for carrying out the assay and usually constant temperatures during the period of the measurement, particularly for rate determinations. Incubation temperatures will normally range from about 5° to 45° C., more usually from about 15° to 40° C. Temperatures during measurements will generally range from about 10° to 50° C., more usually from about 15° to 40° C.

The concentration of analyte which may be assayed will generally vary from about $10^{-4}$ to $10^{-15}$ M, more usually from about $10^{-6}$ to $10^{-13}$ M. Considerations, such as whether the assay is qualitative, semiquantitative or quantitative, the particular detection technique and the concentration of the analyte of interest, will normally determine the concentrations of the other reagents.

While the concentrations of the various reagents in the assay medium will generally be determined by the concentration range of interest of the analyte, the final concentration of each of the reagents will normally be determined empirically to optimize the sensitivity of the assay over the range of interest. That is, a variation in concentration of the analyte which is of significance should provide an accurately measurable signal difference.

The total binding sites of the members of the specific binding pair which are reciprocal to the analyte will vary widely depending upon the nature of the reagents, that is, whether the reagents are the same as or different from the analyte. For example, both reagents may be receptors or both reagents may be ligand or one of the reagents may be ligand and the other reagent receptor. At least one reagent will be the receprocal bonding agent of the analyte.

The ratio of labeled reagent to analyte based on binding sites in the assay medium will generally be from about 0.5 to about 100 binding sites of labeled reagent per binding site of analyte, usually from about 1 to 50, and more usually from about 1 to 20 over the analyte concentration range. These members refer to available sites at saturation since all sites will not be equally available.

It should be appreciated that these numbers are merely intended to be illustrative of the ratios of most likely interest. The ratio will vary depending upon the manner of measurement, equilibrium or rate, the binding constant of the labeled reagent, the concentration of the analyte, the sensitivity of the signal producing system to charge effects, the nature of the ligand, and the sensitivity with which the signal may be detected.

The mole ratio of the charged member to the labeled member may also be varied widely, depending upon the nature of the label, the sensitivity of the label to charge effects, and the nature of the ligand. Usually, the mole ratio of the charged member to the labeled member will be from about 0.5–100:1, more usually from about 1 to 20:1. This can vary quite dramatically, depending upon the particular protocol, the order of addition, the nature of the label, the relative binding affinities and the like.

The order of addition may vary widely, although frequently all of the components of a multicomponent signal producing system will not be added simultaneously. Usually, the member labeled with a component of the signal producing system will be added to the assay medium prior to at least one of the other components of the signal producing system. This will be particularly true, where an enzyme is a label and the other components are substrates and cofactors.

The two reagent members, may be added simultaneously or consecutively to the analyte. Conveniently, the signal producing system label will frequently be added prior to the charged member. The two reagents may be provided as a single composition or as separate compositions, depending upon the nature of the protocol.

Two particular protocols may be indicated as illustrative. The first protocol involves the addition of the signal producing system labeled member to the analyte and incubating for a sufficient time for the system to at least approach equilibrium. To the mixture may then be added the charged member and at the same time or immediately thereafter, any additional components of the signal producing system.

An alternative protocol would be to add substantially simultaneously, the signal producing system labeled member and the charged member and either incubate or not, as required. Desirably, one may add a signal inhibitor; that is, a material which interacts with the signal producing system label, so as to inhibit production of the signal, when the signal producing system labeled member is not bound to its homologous member.

The analyte may act to bring the charged member and the signal label member together or enhance the separation of the charged and signal label members. For example, when the analyte is an antigen or poly(ligand analog) and the two reagent members are antibodies, within a limited concentration range, the analyte will serve to bring on the average the two reagent members in closer proximity than when the members are diffusing freely in solution. On the other hand, when the analyte is an antigen and the signal label member is an antigen, then the analyte and signal label member will compete for a charged antibody.

One or more incubation steps may be involved in preparing the assay medium. For example, it may be desirable to incubate an antigen analyte with labeled receptor. In addition, it may be desirable to have a second incubation step, depending upon the nature of the other reagents employed. Whether to employ an incubation period and the length of the incubation period will depend to a substantial degree on the mode of determination—rate or equilibrium—and the rate of binding of the receptor to the ligand. Usually, the time for incubation steps will vary from about 0.5 min to 6 hrs, more usually from about 5 min to 1 hr. Incubation temperatures will generally range from about 4° to 50° C., more usually from about 15° to 37° C.

After the reagents are combined, the signal will then be determined. The method of determination will normally be the observation of electromagnetic radiation, particularly, ultraviolet and visible light, more particularly visible light, either absorption or emission. Desirably, where fluorescence is involved, the light emitted should have a wavelength in excess of 400 nm, more desirably in excess of 450 nm, and preferably in excess of 500 nm. Where absorption is involved, the absorption will normally be in the range of about 250 to 900 nm, more usually from about 325 to 650 nm.

The temperature at which the signal is observed will generally range from about 10° to 50° C., more usually from about 15° to 40° C.

Standard assay media can be prepared which have known amounts of the analyte. The observed signal for the standard assay media may then be plotted so as to relate concentration to signal. Once a standard curve has been established, a signal may be directly related to the concentration of the analyte.

The time for measuring the signal will vary depending on whether a rate or equilibrium mode is used, the sensitivity required, the nature of the signal producing system and the like. For a rate mode, the times between readings will generally vary from about 5 sec to 6 hrs, usually about 10 sec to 1 hr. For the equilibrium mode, after a steady state is achieved, a single reading may be sufficient or two readings over any convenient time interval may suffice.

DEFINITIONS

Analyte—the compound or composition to be measured, which may be a ligand, a single or plurality of compounds which share at least one common epitopic or determinant site, or a receptor.

Specific binding pair—two different molecules, where one of the molecules has an area on the surface or in a cavity which specifically binds to a particular spatial and polar organization of the other molecule. The members of the specific binding pair are referred to as ligand and receptor (antiligand).

Ligand—any organic compound for which a receptor naturally exists or can be prepared.

Receptor (antiligand)—any compound or composition capable of recognizing a particular spatial and polar organization of a molecule i.e. determinant or epitopic site. Illustrative receptors include naturally occurring receptors, e.g. thyroxine binding globulin, antibodies, Fab fragments, enzymes, lectins and the like.

Ligand Analog—a modified ligand which can compete with the analogous ligand for a receptor, the modification providing means to join the ligand analog to another molecule. Depending upon the available functionalities on the ligand, the ligand analog may differ from the ligand by more than replacement of a hydrogen with a bond which links the ligand analog to a hub or label.

Poly(ligand-analog)—a plurality of ligand analogs joined together covalently, frequently to a hub nucleus. The hub nucleus is a polyfunctional material, normally polymeric, usually having a plurality of functional groups e.g. hydroxy, amino, mercapto, ethylenic, etc. as sites for linking. The hub nucleus may be water soluble or insoluble, usually water soluble, and will normally be at least about 10,000 molecular weight, usually at least about 35,000 molecular weight and may be 10 million or more molecular weight, usually under 600,000, more usually under 300,000 molecular weight. Illustrative hub nuclei include polysaccharides, polypeptides, including proteins, nucleic acids, ion exchange resins and the like. Water insoluble hub nuclei can include glasses, addition and condensation polymers, both cross-linked and non-cross-linked, naturally occurring particles, or the like, either having a plurality of functionalities or capable of functionalization.

Signal Producing System—the signal producing system may have one or more components, there being one component conjugated to a specific binding pair member. The signal producing system produces a measurable signal which is detectible by external means, normally the measurement of electromagnetic radiation. In the subject invention, the level of observed signal produced by the signal producing system will be susceptible to the proximity of the charged member to the labeled member. For the most part, the signal producing system will involve enzymes and chromophores, where chromophores include dyes which absorb light in the ultraviolet or visible region, phosphors, fluorescers and chemiluminescers. The enzymes will normally involve either the formation or destruction of a substance which absorbs light in the ultraviolet or visible region or the direct or indirect production of emitted light by fluorescence or chemiluminescence.

Label—any molecule conjugated to another molecule, particularly, the former being a member of the signal producing system. In the subject invention, the labels will be the signal producing system component bound to a member of the specific binding pair and will be referred to as the signal label.

Labeled Ligand—the conjugate of the ligand member (ligand analog) of the specific binding pair with a member of the signal producing system, either covalently or non-covalently bound, when covalently bound, either bound by a bond, linking group or hub nucleus. The labeled ligand may have one or more ligands or one or more labels or a plurality of both, the latter being referred to as poly(ligand analog)-polylabel.

Labeled Receptor—the conjugate of receptor with a member of the signal producing system, where the two are bound either covalently or noncovalently, usually covalently by a linking group, where there may be one or more receptors bound to the label or one or more labels bound to the receptor.

Charged Member—a soluble member of the specific binding pair, usually the receptor, more usually antibody, being polyionic by being either covalently or non-covalently substituted with a plurality of functionalities of the same charge, either negative or positive, so as to create a relatively high localized density of a particular charge, which may be a single member or a plurality of members linked together.

MATERIALS

The components employed in the subject assay will be the analyte, which is a member of the specific binding pair, the signal labeled member, any additional components of the signal producing system, the charged member, and as appropriate receptor or poly(ligand analog).

Analyte

The ligand analytes of this invention are characterized by being monoepitopic or polyepitopic. The polyepitopic ligand analytes will normally be poly(amino acids) i.e. polypeptides and proteins, polysaccharides, nucleic acids, and combinations thereof. Such combinations of assemblages include bacteria, viruses, chromosomes, genes, mitochondria, nuclei, cell membranes, and the like.

For the most part, the polyepitopic ligand analytes employed in the subject invention will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

The wide variety of proteins may be considered as to the family of proteins having similar structural features, proteins having particular biological functions, proteins related to specific microorganisms, particularly disease causing microorganisms, etc.

The following are classes of proteins related by structure:
    protamines
    histones
    albumins
    globulins
    scleroproteins
    phosphoproteins
    mucoproteins
    chromoproteins
    lipoproteins
    nucleoproteins
    glycoproteins
    proteoglycans
    unclassified proteins, e.g. somatotropin, prolactin, insulin, pepsin A number of proteins found in the human plasma are important clinically and include:
    Prealbumin
    Albumin
    $\alpha_1$-Lipoprotein
    $\alpha_1$-Acid glycoprotein
    $\alpha_1$-Antitrypsin
    $\alpha_1$-Glycoprotein
    Transcortin
    4.6S-Postalbumin
    Tryptophan-poor
        $\alpha_1$-glycoprotein
    $\alpha_1\chi$-Glycoprotein
    Thyroxin-binding globulin
    Inter-$\alpha$-trypsin-inhibitor
    Gc-globulin
        (Gc 1-1)
        (Gc 2-1)
        (Gc 2-2)
    Haptoglobin
        (Hp 1-1)
        (Hp 2-1)
        (Hp 2-2)
    Ceruloplasmin
    Cholinesterase
    $\alpha_2$-Lipoprotein(s)
    Myoglobin
    C-Reactive Protein
    $\alpha_2$-Macroglobulin
    $\alpha_2$-HS-glycoprotein
    Zn-$\alpha_2$-glycoprotein
    $\alpha_2$-Neuramino-glycoprotein
    Erythropoietin
    $\beta$-lipoprotein
    Transferrin
    Hemopexin
    Fibrinogen
    Plasminogen
    $\beta_2$-glycoprotein I
    $\beta_2$-glycoprotein II
    Immunoglobulin G
        (IgG) or $\gamma$G-globulin
    Mol. formula:
        $\gamma_2\kappa_2$ or $\gamma_2\lambda_2$
    Immunoglobulin A (IgA)
        or $\gamma$A-globulin
    Mol. formula:
        $(\alpha_2\kappa_2)^n$ or $(\alpha_2\lambda_2)^n$
    Immunoglobulin M
        (IgM) or $\gamma$M-globulin
    Mol. formula:
        $(\mu_2\kappa_2)^5$ or $(\mu_2\lambda_2)^5$
    Immunoglobulin D(IgD)
        or $\gamma$D-Globulin ($\gamma$D)

| | |
|---|---|
| VII | Proconvertin |
| VIII | Antihemophilic globulin (AHG) |
| IX | Christmas factor, plasma thromboplastin component (PTC) |
| X | Stuart-Prower factor, autoprothrombin III |
| XI | Plasma thromboplastin antecedent (PTA) |
| XII | Hagemann factor |
| XIII | Fibrin-stabilizing factor |

Important protein hormones include:
Peptide and Protein Hormones
    Parathyroid hormone
        (parathromone)
    Thyrocalcitonin Insulin
Glucagon
Relaxin
Erythropoietin
Melanotropin
   (melanocyte-stimulating hormone; intermedin)
Somatotropin
   (growth hormone)
Corticotropin
   (adrenocorticotropic hormone)
Thyrotropin
Follicle-stimulating hormone
Luteinizing hormone
   (interstitial cell-stimulating hormone)
Luteomammotropic hormone
   (luteotropin, prolactin)
Gonadotropin
   (chorionic gonadotropin)
Tissue Hormones
   Secretin
   Gastrin
   Angiotensin I and II
   Bradykinin
   Human placental lactogen
Peptide Hormones from the Neurohypophysis
   Oxytocin
   Vasopressin
   Releasing factors (RF)
      CRF, LRF, TRF, Somatotropin-RF,
      GRF, FSH-RF, PIF, MIF Other polymeric materials of interest are mucopolysaccharides and polysaccharides.

Illustrative antigenic polysaccharides derived from microorganisms are as follows:

| Species of Microorganisms | Hemosensitin Found in |
|---|---|
| Streptococcus pyogenes | Polysaccharide |
| Diplococcus pneumoniae | Polysaccharide |
| Neisseria meningitidis | Polysaccharide |
| Neisseria gonorrheae | Polysaccharide |
| Corynebacterium diphtheriae | Polysaccharide |
| Actinobacillus mallei; | Crude extract |
| Actinobacillus whitemori | |
| Francisella tularensis | Lipopolysaccharide Polysaccharide |
| Pagteurella pestis | |
| Pasteurella pestis | Polysaccharide |
| Pasteurella multocida | Capsular antigen |
| Brucella abortus | Crude extract |
| Haemophilus influenzae | Polysaccharide |
| Haemophilus pertussis | Crude |
| Treponema reiteri | Polysaccharide |
| Veillonella | Lipopolysaccharide |
| Erysipelothrix | Polysaccharide |
| Listeria monocytogenes | Polysaccharide |
| Chromobacterium | Lipopolysaccharide |
| Mycobacterium tuberculosis | Saline extract of 90% phenol extracted mycobacteria and polysaccharide fraction of cells and turberculin |
| Klebsiella aerogenes | Polysaccharide |
| Klebsiella cloacae | Polysaccharide |
| Salmonella typhosa | Lipopolysaccharide, Polysaccharide |
| Salmonella typhi-murium; | Polysaccharide |

-continued

| Species of Microorganisms | Hemosensitin Found in |
|---|---|
| Salmonella derby | |
| Salmonella pullorum | |
| Shigella dysenteriae | Polysaccharide |
| Shigella flexneri | |
| Shigella sonnei | Crude, Polysaccharide |
| Rickettsiae | Crude extract |
| Candida albicans | Polysaccharide |
| Entamoeba histolytica | Crude extract |

The microorganisms which are assayed may be intact, lysed, ground or otherwise fragmented, and the resulting composition or portion, e.g by extraction, assayed. Microorganisms of interest include:

Corynebacteria
   Corynebacterium diptheriae
Pneumococci
   Diplococcus pneumoniae
Streptococci
   Streptococcus pyogenes
   Streptococcus salivarus
Staphylococci
   Staphylococcus aureus
   Staphylococcus albus
Neisseriae
   Neisseria meningitidis
   Neisseria gonorrheae
Enterobacteriaciae

| Escherichia coli | } The coliform bacteria |
|---|---|
| Aerobacter aerogenes | |
| Klebsiella pneumoniae | |
| Salmonella typhosa | } The Salmonellae |
| Salmonella choleraesuis | |
| Salmonella typhimurium | |
| Shigella dysenteriae | } The Shigellae |
| Shigella schmitzii | |
| Shigella arabinotarda | |
| Shigella flexneri | |
| Shigella boydii | |
| Shigella sonnei | |

Other enteric bacilli

| Proteus vulgaris | } Proteus species |
|---|---|
| Proteus mirabilis | |
| Proteus morgani | |

Pseudomonas aeruginosa
Alcaligenes faecalis
Vibrio cholerae
Hemophilus-Bordetella group
   Hemophilus influenzae,
      H. ducreyi
      H. hemophilus
      H. aegypticus
      H. parainfluenzae
   Bordetella pertussis
Pasteurellae
   Pasteurella pestis
   Pasteurella tulareusis
Brucellae
   Brucella melitensis
   Brucella abortus
   Brucella suis
Aerobic Spore-forming Bacilli
   Bacillus anthracis

*Bacillus subtilis*
*Bacillus megaterium*
*Bacillus cereus*
Anaerobic Spore-forming Bacilli
  *Clostridium botulinum*
  *Clostridium tetani*
  *Clostridium perfringens*
  *Clostridium novyi*
  *Clostridium septicum*
  *Clostridium histolyticum*
  *Clostridium tertium*
  *Clostridium bifermentans*
  *Clostridium sporogenes*
Mycobacteria
  *Mycobacterium tuberculosis hominis*
  *Mycobacterium bovis*
  *Mycobacterium avium*
  *Mycobacterium leprae*
  *Mycobacterium paratuberculosis*
Actinomycetes (fungus-like bacteria)
  *Actinomyces israelii*
  *Actinomyces bovis*
  *Actinomyces naeslundii*
  *Nocardia asteroides*
  *Nocardia brasiliensis*
The Spirochetes
  *Treponema palladium; Spirillum minus*
  *Treponema pertenue; Streptobacillus moniliformis*
  *Treponema carateum*
  *Borrelia recurrentis*
  *Leptospira icterohemorrhagiae*
  *Leptospira canicola*
Mycoplasmas
  *Mycoplasma pneumoniae*
Other pathogens
  *Listeria monocytogenes*
  *Erysipelothrix rhusiopathiae*
  *Streptobacillus moniliformis*
  *Donvania granulomatis*
  *Bartonella bacilliformis*
Rickettsiae (bacteria-like parasites)
  *Rickettsia prowazekii*
  *Rickettsia mooseri*
  *Rickettsia rickettsii*
  *Rickettsia conori*
  *Rickettsia australis*
  *Rickettsia sibiricus*
  *Rickettsia akari*
  *Rickettsia tsutsugamushi*
  *Rickettsia burnetti*
  *Rickettsia quintana*
Chlamydia (unclassifiable parasites bacterial/viral)
  Chlamydia agents (naming uncertain)
Fungi
  *Cryptococcus neoformans*
  *Blastomyces dermatidis*
  *Histoplasma capsulatum*
  *Coccidioides immitis*
  *Paracoccidioides brasiliensis*
  *Candida albicans*
  *Aspergillus fumigatus*
  *Mucor corymbifer (Absidia corymbifera)*

| | |
|---|---|
| *Rhizopus oryzae* <br> *Rhizopus arrhizus* <br> *Rhizopus nigricans* | } Phycomycetes |

*Sporotrichum schenkii*
  *Fonsecaea pedrosoi*
  *Fonsecaea compacta*
  *Fonsecaea dermatidis*
  *Cladosporium carrionii*
  *Phialophora verrucosa*
  *Aspergillus nidulans*
  *Madurella mycetomi*
  *Madurella grisea*
  *Allescheria boydii*
  *Phialosphora jeanselmei*
  *Microsporum gypseum*
  *Trichophyton mentagrophytes*
  *Keratinomyces ajelloi*
  *Microsporum canis*
  *Trichophyton rubrum*
  *Microsporum andouini*
Viruses
Adenoviruses
Herpes Viruses
  *Herpes simplex*
  Varicella (Chicken pox)
  *Herpes Zoster* (Shingles)
  Virus B
  Cytomegalovirus
Pox Viruses
  Variola (smallpox)
  Vaccinia
  Poxvirus bovis
  Paravaccinia
  *Molluscum contagiosum*
Picornaviruses
  Poliovirus
  Coxsackievirus
  Echoviruses
  Rhinoviruses
Myxoviruses
  Influenza (A, B, and C)
  Parainfluenza (1–4)
  Mumps Virus
  Newcastle Disease Virus
  Measles Virus
  Rinderpest Virus
  Canine Distemper Virus
  Respiratory Syncytial Virus
  Rubella Virus
Arboviruses
  Eastern Equine Eucephalitis Virus
  Western Equine Eucephalitis Virus
  Sindbis Virus
  Chikugunya Virus
  Semliki Forest Virus
  Mayora Virus
  St. Louis Encephalitis Virus
  California Encephalitis Virus
  Colorado Tick Fever Virus
  Yellow Fever Virus
  Dengue Virus
Reoviruses
  Reovirus Types 1–3
Hepatitis
  Hepatitis A Virus
  Hepatitis B Virus
Tumor Viruses
  Rauscher Leukemia Virus
  Gross Virus
  Maloney Leukemia Virus The monoepitopic ligand analytes will generally be from about 100 to 2,000 molecular weight, more usually from 125 to 1,000 molecular weight. The analytes of interest include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which includes cocaine and benzoyl ecgonine, their derivatives and metabolites; ergot alkaloids, which includes the diethylamide of lysergic acid; steroid alkaloids; iminazoyl alkaloids; quinazoline alkaloids, isoquinoline alkaloids; quinoline alkaloids; which includes quinine and quinidine; diterpene alkaloids; their derivatives and metabolites.

The next group of drugs includes steroids, which includes the estrogens, gestogens, androgens, andrenocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular members, which include the barbiturates, e.g. phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines, catecholamines, which includes ephedrine, L-dopa, epinephrine, narceine, papaverine, their metabolites.

The next group of drugs is aminoalkylbenzenes, with alkyl of from 2 to 3 carbon atoms, which includes ephedrine, L-dopa, epinephrine, narceine, papverine, their metabolites and derivatives.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, e.g. $B_{12}$, C, D, E and K, folic acid, thiamine.

The next group of drugs is prostaglandins, which differ by the degree and sites of hydroxylation and unsaturation.

The next group of drugs is antibiotics, which include penicillin, chloromycetin, actinomycetin, tetracycline, terramycin, their metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propranolol, griseofulvin, valproic acid, butyrophenones, antihistamines, anticholinergic drugs, such as atropine, their metabolites and derivatives.

The next group of compounds is amino acids and small peptides, which include polyiodothyronines e.g. thyroxine, and triiodothyronine, oxytocin, ACTH, angiotensin, met- and leu-enkephalin their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2 \times 10^6$, more usually from 10,000 to $10^6$. For immunoglobulins, IgA, IgG, IgE and IgM, the molecular weights will generally vary from about 160,000 to about $10^6$. Enzymes will normally range from about 10,000 to 6000,000 in molecular weight. Natural receptors vary widely, generally being at least about 25,000 molecular weight and may be $10^6$ or higher molecular weight, including such materials as avidin, thyroxine binding globulin, thyroxine binding prealbumin, transcortin, etc.

Ligand Analog

The ligand analog will differ from the ligand either by replacement of a hydrogen or a functionality with a bond or a linking group which has a functionality for forming a covalent bond to another molecule having an active functionality, such as an hydroxyl, amino, aryl, thio, olefin, etc., where the resulting compound differs from the ligand by more than substitution of a hydrogen by the molecule to which it is conjugated. The linking group will normally have from 1-20 atoms other than hydrogen, which are carbon, oxygen, sulfur, nitrogen, and halogen of atomic number 17-35. The functionalities which are involved include carbonyl, both oxo and nonoxo, active halogen, diazo, mercapto, ethylene, particularly activated ethylene, amino, and the like. The number of heteroatoms will generally range from about 0-6, more usually from about 1-6, and preferably from about 1-4. A description of linking groups may be found in U.S. Pat. No. 3,817,837, which disclosure is incorporated herein by reference.

For the most part, the linking groups will be aliphatic, although with diazo groups, aromatic groups are involved. Generally, the linking group is a divalent chain having about 1-10, more usually from about 1-6 atoms in the chain. Oxygen will normally be present as oxo or oxy, bonded to carbon and hydrogen, preferably bonded solely to carbon, while nitrogen will normally be present as amino, bonded solely to carbon, or amido, while sulfur would be analogous to oxygen.

Common functionalities in forming the covalent bond between the linking group and the molecule to be conjugated are alkylamine, amide, amidine, thioamide, urea, thiourea, guanidine, and diazo.

Linking groups which find particular application with conjugation to polypeptides are those involving carboxylic acids which may be used in conjunction with diimides, or as mixed anhydrides with carbonate monesters or as active carboxylic esters e.g. N-hydroxy succinimide or p-nitrophenyl. Nitrogen analogs may be employed as imidoesters. Aldehydes can be used to form imines under reductive amination conditions e.g. in the presence of borohydrides, to produce alklyamines. Other non-oxo carbonyl groups which may be employed include isocyanates and isothiocyanates. In addition, active halide may be employed, particularly bromoacetyl groups.

In most instances, the ligand will have one or more functional groups which may be employed as the site for linking the linking group. Particularly, hydroxy, amino and aryl groups, particularly activated aryl groups find use. Also, oximes may be prepared from oxo functionalities and the hydroxyl used as a site for joining to a linking group, such as carboxymethyl.

The choice of linking group will vary widely, depending upon the functionalities which are present in the ligand, in the compound to which the ligand is to be conjugated, the nature and length of the linking group desired, and the like.

Signal Producing System

The signal producing system will have at least one member and provide a detectible signal in the assay medium, which signal will be influenced by the proximity of the highly charged molecule to the labeled member. Besides being suspectible to the presence of the highly charged molecule, it is desirable that the signal producing system provide for several measurable events in response to the binding between the members of a single specific binding pair (amplification).

The signal producing systems of primary interest are those involving a catalyst, particularly an enzymatic catalyst, or a chromophore which absorbs or emits light, particularly fluorescers and chemiluminescers, as well as combinations of the two systems.

The first type of system to be considered will be those involving enzymes.

Enzymes

The first consideration in choice of an enzyme for the subject invention is that it can be influenced by the proximity of the highly charged molecule. The highly charged molecule can influence the enzyme in at least one of three different ways. The first way is by influencing the localized concentration of protons. The localized concentration of protons (reciprocally the hydroxide concentration) affects the enzyme activity by affecting the conformation of the enzyme or the degree of ionization of specific functionalities of the enzyme or substrate essential to the reaction, i.e. protonated or unprotonated. Therefore, one can obtain a rate enhancement or rate reduction depending upon the pH of the bulk solution, the nature of the charged species and the enzyme response to the local proton concentration.

A second manner in which the enzyme rate can be affected is by the attraction or repulsion of a charged substrate, particularly a substrate which has a plurality of substrate molecules bonded to a hub. The charged member when in proximity to the signal label, i.e. enzyme, can attract or repel the substrate, so as to enhance or reduce the rate of turnover.

A third technique is to have a charged substance which can affect the localized concentration of a compound which interacts with an enzyme product. For example, where an enzyme produces a chemiluminescent reaction, one could provide a charged energy acceptor which is attracted by the charged member, and the energy from the chemiluminescer would be transferred to the energy acceptor in close proximity to the chemiluminescer with resulting sensitized emission from the acceptor.

In choosing an enzyme, in addition to the effect of the charged particle on the enzyme turnover rate, other considerations will also affect the choice of enzyme. These considerations include the stability of the enzyme, the desirability of a high turnover rate, the sensitivity of the rate to variations in the physical environment, the nature of the substrate(s) and product(s), particularly the ability to accurately measure the substrate or product, preferably the product, the availability of the enzyme, the effect of conjugation of the enzyme on the enzyme's properties, the effect on enzyme activity of materials which may be encountered in the sample solutions, the molecular weight of the enzyme, and the like. The following are categories of enzymes as set forth in accordance with the classification of the International Union of Biochemistry.

TABLE 1

1. Oxiodoreductases
   1.1 Acting on the CH—OH group of donors
      1.1.1 With NAD or NADP as acceptor
      1.1.2 With a cytochrome as an acceptor
      1.1.3 With $O_2$ as acceptor
      1.1.99 With other acceptors
   1.2 Acting on the aldehyde or keto group of donors
      1.2.1 With NAD or NADP as acceptor
      1.2.2 With cytochrome as an acceptor
      1.2.3 With $O_2$ as acceptor
      1.2.4 With lipoate as acceptor
      1.2.99 With other acceptors
   1.3 Acting on the CH—CH group of donors
      1.3.1 With NAD or NADP as acceptors
      1.3.2 With a cytochrome as an acceptor
      1.3.3 With $O_2$ as acceptor
      1.3.99 With other acceptors
   1.4 Acting on the CH—$NH_2$ group of donors
      1.4.1 With NAD or NADP as acceptor
      1.4.3 With $O_2$ as acceptor
   1.5 Acting on the C—NH group of donors
      1.5.1 With NAD or NADP as acceptor
      1.5.3 With $O_2$ as acceptor
   1.6 Acting on reduced NAD or NADP as donor
      1.6.1 With NAD or NADP as acceptor
      1.6.2 With a cytochrome as an acceptor
      1.6.4 With a disulfide compound as acceptor
      1.6.5 With a quinone or related compound as acceptor
      1.6.6 With a nitrogeneous group as acceptor
      1.6.99 With other acceptors
   1.7 Acting on other nitrogeneous compounds as donors
      1.7.3 With $O_2$ as acceptor
      1.7.99 With other acceptors
   1.8 Acting on sulfur groups of donors
      1.8.1 With NAD or NADP as acceptor
      1.8.3 With $O_2$ as acceptor
      1.8.4 With a disulfide compound as acceptor
      1.8.5 With a quinone or related compound as acceptor
      1.8.6 With nitrogeneous group as acceptor
   1.9 Acting on heme groups of donors
      1.9.3 With $O_2$ as acceptor
      1.9.6 With a nitrogeneous group as acceptor
   1.10 Acting on diphenols and related substances as donors
      1.10.3 With $O_2$ as acceptors
   1.11 Acting on $H_2O_2$ as acceptor
   1.12 Acting on hydrogen as donor
   1.13 Acting on single donors with incorporation of oxygen (oxygenases)
   1.14 Acting on paired donors with incorporation of oxygen into one donor (hydroxylases)
      1.14.1 Using reduced NAD or NADP as one donor
      1.14.2 Using ascorbate as one donor
      1.14.3 Using reduced pteridine as one donor 2. Transferases
  2.1 Transferring one-carbon groups
    2.1.1 Methyltransferases
    2.1.2 Hydroxymethyl-, formyl- and related transferases
    2.1.3 Carboxyl- and carbamoyltransferases
    2.1.4 Amidinotransferases
  2.2 Transferring aldehydic or ketonic residues
  2.3 Acyltransferases
    2.3.1 Acyltransferases
    2.3.2 Aminoacyltransferases
  2.4 Glycosyltransferases
    2.4.1 Hexosyltransferases
    2.4.2 Pentosyltransferases
  2.5 Transferring alkyl or related groups
  2.6 Transferring nitrogenous groups
    2.6.1 Aminotransferases
    2.6.3 Oximinotransferases
  2.7 Transferring phosphorus-containing groups
    2.7.1 Phosphotransferases with an alcohol group as acceptor
    2.7.2 Phosphotransferases with a carboxyl group as acceptor
    2.7.3 Phosphotransferases with a nitrogeneous group as acceptor
    2.7.4 Phosphotransferases with a phosphogroup as acceptor
    2.7.5 Phosphotransferases, apparently intromolecular
    2.7.6 Pyrophosphotransferases
    2.7.7 Nucleotidyltransferases
    2.7.8 Transferases for other substituted phosphogroups
  2.8 Transferring sulfur-containing groups
    2.8.1 Sulfurtransferases
    2.8.2 Sulfotransferases
    2.8.3 CoA-transferases
3. Hydrolases
  3.1 Acting on ester bonds
    3.1.1 Carboxylic ester hydrolases
    3.1.2 Thiolester hydrolases
    3.1.3 Phosphoric monoester hydrolases
    3.1.4 Phosphoric diester hydrolases
    3.1.5 Triphosphoric monoester hydrolases
    3.1.6 Sulfuric ester hydrolases
  3.2 Acting on glycosyl compounds
    3.2.1 Glycoside hydrolases
    3.2.2 Hydrolyzing N-glycosyl compounds
    3.2.3 Hydrolizing S-glycosyl compounds
  3.3 Acting on ether bonds
    3.3.1 Thioether hydrolases
  3.4 Acting on peptide bonds (peptide hydrolases)
    3.4.1 α-Aminoacyl-peptide hydrolases
    3.4.2 Peptidyl-aminoacid hydrolases
    3.4.3 Dipeptide hydrolases
    3.4.4 Peptidyl-peptide hydrolases
  3.5 Acting on C—N bonds other than peptide bonds
    3.5.1 In linear amides
    3.5.2 In cyclic amides
    3.5.3 In linear amidines
    3.5.4 In cyclic amidines
    3.5.5 In cyanides
    3.5.99 In other compounds
  3.6 Acting on acid-anhydride bonds
    3.6.1 In phosphoryl-containing anhydrides
  3.7 Acting on C—C bonds
    3.7.1 In ketonic substances
  3.8 Acting on halide bonds
    3.8.1 In C-halide compounds
    3.8.2 In P-halide compounds
  3.9 Acting on P-N bonds
4. Lyases
  4.1 Carbon-carbon lyases
    4.1.1 Carboxy-lyases
    4.1.2 Aldehyde-lyases
    4.1.3 Ketoacid-lyases
  4.2 Carbon-oxygen lyases
    4.2.1 Hydro-lyases
    4.2.99 Other carbon-oxygen lyases
  4.3 Carbon-nitrogen lyases
    4.3.1 Ammonia-lyases
    4.3.2 Amidine-lyases
  4.4 Carbon-sulfur lyases
  4.5 Carbon-halide lyases
  4.99 Other lyases
5. Isomerases
  5.1 Racemases and epimerases
    5.1.1 Acting on amino acids and derivatives
    5.1.2 Acting on hydroxy acids and derivatives
    5.1.3 Acting on carbohydrates and derivatives
    5.1.99 Acting on other compounds
  5.2 Cis-trans isomerases
  5.3 Intramolecular oxidoreductases
    5.3.1 Interconverting aldoses and ketoses
    5.3.2 Interconverting keto and enol groups
    5.3.3 Transposing C=C bonds
  5.4 Intramolecular transferases
    5.4.1 Transferring acyl groups
    5.4.2 Transferring phosphoryl groups
    5.4.99 Transferring other groups
  5.5 Intramolecular lyases
  5.99 Other isomerases
6. Ligases or Synthetases
  6.1 Forming C—O bonds
    6.1.1 Aminoacid-RNA ligases
  6.2 Forming C—S bonds
    6.2.1 Acid-thiol ligases
  6.3 Forming C—N bonds
    6.3.1 Acid-ammonia ligases (amide synthetases)
    6.3.2 Acid-aminoacid ligases (peptide synthetases)
    6.3.3 Cyclo-ligases
    6.3.4 Other C—N ligases
    6.3.5 C—N ligases with glutamine as N-donor
  6.4 Forming C—C bonds Of particular interest will be enzymes which are in Class 1. Oxidoreductases and Class 3 hydrolases, although enzymes of Class 2, Transferases, Class 4 Lyases and Class 5, Isomerases, can also be of interest in particular situations.

The following table has specific subclasses of enzymes and specific enzymes within the subclass which are of particular interest. Among the oxidoreductases, those involving NAD or NADP, oxygen or hydrogen peroxide are of particular interest. Among the hydrolases, those involving phosphate and glycosides are of particular interest.

TABLE 2

1. Oxidoreductases
  1.1 Acting on the CH—OH group of donors
    1.1.1 With NAD or NADP as acceptor
      1. alcohol dehydrogenase
      6. glycerol dehydrogenase
      27. lactate dehydrogenase
      37. malate dehydrogenase
      49. glucose-6-phosphate dehydrogenase 1.1.3 With O₂ as acceptor
   4. glucose oxidase galactose oxidase
1.2 Acting on the aldehyde or keto group of donors
   1.2.1 With NAD or NADP as acceptor
      12. glyceraldehyde-3-phosphate dehydrogenase
   1.2.3 With O₂ as acceptor
      2. xanthine oxidase luciferase
1.4 Acting on the CH—NH₂ group of donors
   1.4.3 With O₂ as acceptor
      2. L-amino acid oxidase
      3. D-amino acid oxidase
1.6 Acting on reduced NAD or NADP as donor
   1.6.99 With other acceptors diaphorase
1.7 Acting on other nitrogeneous compounds as donors
   1.7.3 With O₂ as acceptor
      3. Uricase
1.11 Acting on H₂O₂ as acceptor
   1.11.1
      6. catalase
      7. peroxidase
2. Transferases
   2.7 Transferring phosphorus-containing groups
      2.7.1 Phosphotransferases with CH—OH as acceptor
         1. hexokinase
         2. glucokinase
         15. ribokinase
         28. triokinase
         40. pyruvate kinase
      2.7.5 1. phosphoglucomutase
3. Hydrolases
   3.1 Acting on ester bonds
      3.1.1 Carboxylic ester hydrolases
         7. cholinesterase
         8. pseudo cholinesterase
      3.1.3 Phosphoric monoester hydrolases
         1. alkaline phosphatase
         2. acid phosphatase
         9. glucose-6-phosphatase
         11. fructose diphosphatase
      3.1.4 Phosphoric diester hydrolases
         1. phosphodiesterase
         3. phospholipase C
   3.2 Acting on glycosyl compounds
      3.2.1 Glycoside hydrolases
         1. alpha amylase
         2. beta amylase
         4. cellulase
         17. muramidase
         18. neuraminidase
         21. beta glucosidase
         23. beta galactosidase
         31. beta glucuronidase
         35. hyaluronidase
      3.2.2 Hydrolyzing N-glycosyl compounds
         5. DPNase
4. Lyases
   4.1 Carbon-carbon lyases
      4.1.2 Aldehyde lyases
         13. aldolyase
   4.2.1 Hydro-lyases
      1. carbonic anhydrase
5. Isomerase
   5.4 Intramolecular transferases
      5.4.2 Transferring phosphoryl group triose phosphate isomerase Besides enzymes as labels, one can also employ chromogenic materials as labels, particularly compounds which absorb light in the ultraviolet or visible region, fluoresce or chemiluminesce, particularly fluoresce. The chromogenic member must provide a signal which can be affected by the presence of the charged member. This will normally involve the enhancement or diminution of a charged species, where the charged species has an enhanced or diminished signal capability. For example, if the negative ionic form of a fluorescer is necessary for fluorescence, it would be desirable to have a positively charged member adjacent to the fluorescer to stabilize the negatively charged form. By buffering the system so as to favor the unionized form of the fluorescer, the concentration of the ionized form of the fluorescer would be enhanced by the enhanced proximity of the fluorescer to the positively charged member. By employing chromogenic substances which can donate or receive a proton in aqueous media at a pH in the range of about 4 to 11, where the chromophoric properties of the protonated form are substantially different from the unprotonated form, the presence of the charged member can be used to influence the observed signal.

Fluorescers of interest fall into a variety of categories having certain primary functionalities. The amino substituted fluorescers include 1- and 2-aminonaphthalene, p,p'-diaminostilbenes, 9-aminoacridines, p,p'-diaminobenzophenone imines, bis-3-aminopyridinium salts, and indoles. Acidic, normally phenolic fluorescers, include 7-hydroxycoumarin, 2,7-dihydroxyxanthenes, sterophenol, tetracycline, and salicylate.

An alternative source of light as a detectible signal is a chemiluminescent source. The chemiluminescent source involves a compound which becomes electronically excited by a chemical reaction and may then emit light which serves as the detectible signal or donates energy to an energy acceptor, which in turn may fluoresce.

A diverse number of families of compounds have been found to provide chemiluminescence under a variety of conditions. One family of compounds is 2,3-dihydro-1,4-phthalazinedione of which luminol is the most popular member. Another group of compounds includes the 2,4,5-triphenylimidazoles.

These compounds can be utilized individually as affected by the charged member or can be modified to be employed as enzyme substrates, where the enzyme is affected by the charged member, so that the turnover rate for transformation of the chromophoric substrate will be affected. A broader spectrum of chromophores may then be employed, depending upon the nature of the enzyme and the particular linking group required for modification by the enzyme.

For example, hydrolase enzymes may be employed with esters of phenol containing chromogens where the chromogenic properties of the ester are substantially different from the chromogenic properties of the phenol. The rate of production of the hydrolysed chromogen can be influenced by the proximity of the charged member. Illustrative compounds are fluorescein diphosphate, umbelliferyl phosphate, or the like.

Signal Labeled Member

The signal label may be conjugated to either the ligand or receptor. When the ligand is a hapten or small molecule, normally the hapten will be conjugated to an enzyme label, so that the charged member can either enhance or diminish the activity of the enzyme when bound to the hapten. Where the ligand is a hapten and the signal label is other than an enzyme, while a single haptenic ligand may be linked to a fluorescer or chemiluminescer, usually one will prepare a poly(ligand analog)-label so as to have a plurality of binding sites which can result in bringing at least one charged member into proximity with said labels.

For antigenic molecules, which are normally polyepitopic, the situation where the signal label is a large molecule such as an enzyme, will be different from when the signal label is a small molecule such as a fluorescer. Where the signal label is a large molecule such as an enzyme, and one is dealing with a relatively impure mixture containing either the ligand or receptor, one will normally provide for a plurality of substituents on the signal label, to provide some assurance that most of the signal label is bonded to either the ligand or receptor of interest. Desirably, at least half, more usually at least three-quarter and preferably at least about one member of the specific binding pair is bonded to the signal label on the average. Thus, while the signal label may be polysubstituted, for the most part, it will be generally at least monosubstituted with a member of the specific binding pair.

This polysubstitution with impure mixtures of a member of the specific binding pair is to minimize background effects. That is, if one employed an impure mixture of receptor, for example, and conjugated it to enzyme, if there was a one to one mole ratio of molecules in the impure mixture to molecules of enzyme, a substantial proportion of the enzyme would only be bound to impurities and if active would be capable of providing a substantial background. To insure that substantially all of the signal label is capable of binding to the homologous pair member, impure mixtures of a member of the specific binding pair will be substituted in such a way as to substantially insure that at least one member of the specific binding pair is bonded to the enzyme.

Where the signal label is small, a different situation is encountered. Here, a plurality of the members of the specific binding pair cannot be bonded to a signal label, so that when the ligand or receptor is impure there will be a substantial amount of label bound only to impurities. In this situation, it will normally be desirable that under the conditions of the assay, the signal label bonded to contaminants provides a minimum signal or no signal, or some technique is provided whereby the signal label bonded to contaminants is inhibited from providing a signal.

The ratio of signal label to member of the specific binding pair will vary widely depending upon the signal label, the member of the specific binding pair, the required sensitivity of the assay, the ability to inhibit background, the effect of the signal label on the characteristics of the member of the specific binding pair, and the like.

To further enhance the signal level difference between the signal level when the signal label is in close proximity to the charged member as compared to when they are far apart, the signal labeled member may be modified to introduce charges opposite to the charged member. On the average, there will be at least about 0.5 charge per signal label, preferably at least about 1, and usually not more than about 50, more usually not more than about 10 charges per signal label. The signal labeled member can be modified in the same manner and with the same kind of ionizable substituents as the charged member. While some reduction of the maximum signal may result from the presence of charges on the signal label member, it is found that there is a greater separation between the signals observed from the signal label in the presence and absence of the charged member.

Charged Member

The charged member will either be a ligand or receptor, more usually a receptor, and generally proteinaceous. When a receptor, the molecular weight will vary from about 5,000 to two million or higher, but will usually be antibody of about 160,000 to 800,000 molecular weight.

The number of functionalities which are introduced which can provide a charge, either by being permanently charged or capable of receiving or donating a proton to the solvent medium, will generally be not less than about one per 20,000 molecular weight and not more than about one per 500 molecular weight, more usually being about one to from about 1,000 to 10,000 molecular weight. That is, the equivalent weight per charge will be at least about 500, usually from 1,000 to 10,000 and not less than about 20,000.

Various functionalities can be employed which have the capability of providing a stable charge in the assay medium. Illustrative groups include basic nitrogen, such as amines, quaternary ammonium salts, phosphonium salts, tetrazolium salts, onium salts, hydrazine salts, metal chelates, etc. Negative functionalities include carboxylates, sulfur acids, such as sulfonates and sulfates, phosphorus acids, such as phosphonates and phosphates, oxides, such as phenolics, mercaptides, or the like.

Of particular interest are ionizable oxy groups, that is, functionalities having an ionizable hydroxylic group as in the oxy acids indicated above.

The functionalities will be bonded by any convenient linking group, generally of from about one to ten carbon atoms, which has an appropriate functionality for forming a covalent bond to the member of the specific binding pair. Of course, one should not destroy a group providing a charge to introduce another group providing the same charge, as for example, substituting an amino group with an amino acid to form the amino amide. However, one could use a polyamine to substitute a single amine group, as in the situation where one prepares the maleimide of an amino group and conjugates a polyaminomercaptan where a single amino group results in a plurality of amino groups. The particular manner of linking, the choice of linking groups and functionalities, and the particular functionality employed to provide the charge is not critical to this invention, and a wide variety of charged members may be employed.

Particularly useful anionic compositions are antibodies substituted with di- or polybasic acids, particularly diacids of from about 4 to 10 carbon atoms, which diacids may be aliphatic, alicyclic or aromatic. Illustrative dibasic acids which may be used include succinic, glutaric, maleic, phthalic, hexahydrophthalic, etc. which form the respective amic acids upon reaction with an antibody.

Signal Inhibitors

In order to minimize background, it may be desirable to add a signal inhibitor to the system, where the inhibitor is prevented from interacting with the signal label when involved in an immunocomplex resulting from the binding of the members of the specific binding pair, but will interact with the signal label which is not in the immunocomplex. Usually, such inhibitors will be macromolecules, which are sterically inhibited from approaching the signal label when the label is involved with the binding of at least two members of the specific binding pair. Illustrative macromolecules include antilabel, such as antienzyme and antifluorescer, where the turnover rate of the enzyme and the fluorescence efficiency are respectively substantially diminished. In addition, chemical enzyme inhibitors can be bound to macromolecules to inhibit the enzyme, or antifluorescers may be modified by binding quenchers to the antifluorescer, such as energy acceptors or heavy atoms, or the like. The amount of the inhibitor which will be added will be sufficient to substantially reduce the signal produced by the background, so as to limit the observed signal to the signal label involved in the complex formed by the binding of the homologous members of the specific binding pairs.

Ancillary Components

In addition to the reagents described above, depending upon the nature of the signal label, additional components will be included, such as enzyme substrates, cofactors, salts, detergents, stabilizers, buffers or the like. Frequently, in order to maximize charge interactions, the substrate will be linked to a macromolecule providing for a plurality of charges, either attracted to or repelled by the charges of the charged member. Therefore, various substrates will be employed where the hub nucleus provides a plurality of charges, where the substrate itself is charged or uncharged.

By appropriate choice of a hub nucleus, the hub nucleus may provide the desired charge density for interacting with the charged member. The ionic equivalent weight may be as low as 100 and will usually be not greater than 20,000, usually not greater than 10,000.

Illustrative monomers which may be employed for preparing polymers and which provide for ions in the assay medium, which monomers may be used by themselves or in conjunction with neutral monomers include aziridine, N-(2'-aminoethyl)acrylamide, acrylic acid, methacrylic acid, maleic anhydride, vinyl sulfonate, vinyl phosphate, aminomethylstyrene, and the like. Usually the ionic monomer will be from about 1 to 50, more usually 1 to 25 mol percent of the copolymer.

Alternatively, ionic condensation polymers may be employed such as carboxymethyl cellulose, polylysine, polypeptides containing a plurality of basic amino acids e.g. lysine, arginine, and histidine or acidic amino acids e.g. aspartic acid and glutamic acid.

Where the hub nucleus is neutral, charged groups may be attached or a charged spacer arm can be employed with a neutral substrate. Various spacer arms may be used which provide for an ionic charge, such as polyamines, particularly having tertiary amines in the chain e.g. bis-2-aminoethylmethylamine and bis-N,N'-2-aminoethylpiperazine, or polyacids, such as 1,3,5-pentantricarboxylic acid or 3,6-dithia-1,2,7,8-octantetracarboxylic acid.

Assay Combinations

To enhance the versatility of the subject method, the reagents can be provided in combination, in the same or separate vials, so that the ratio of the reagents provides for substantial optimization of the signal response to variations in analyte concentration. Included with the reagents may be such ancillary components as buffer, stabilizers, detergents, or the like.

Compounds

Novel compounds are provided which are antibodies to which are bonded a plurality of functionalities capable of providing charges under the assay conditions, namely at a pH in the range of about 4 to 11, more usually in the range of about 5 to 10, and preferably in the range of about 6.5 to 9.5. For the most part, the compositions will have the following formula.

1. Receptor–(RX)$_n$ wherein:

Receptor is a specific receptor for another molecule, is proteinaceous, normally an antibody;

R is a bond or linking group, normally of from about one to ten, usually of from about one to six carbon atoms and may have from zero to six, usually zero to four heteroatoms, which are oxygen, nitrogen, or sulfur, wherein oxygen is present as oxy or oxo, nitrogen is present as amino or amido, and sulfur is present as thio or thiono;

X is a functionality capable of having a charge at a pH in the range of about 4 to 11, usually 5 to 10, and preferably 6.5 to 9.5, and can be amino or an oxy acid, including carboxy, sulfonate, sulfate, phosphonate, phosphate, and phenoxy; and n is at least one and is normally in the range of the molecular weight of Receptor divided by 20,000 to the molecular weight of Receptor divided by 500, more usually in the range of the molecular weight of Receptor divided by 10,000 to the molecular weight of Receptor divided by 1,000.

Particularly, Receptor is antibody, IgG, R is 1-oxoalkylene, the oxo group forming an amide bond, and the alkylene group is of from two to six carbon atoms, usually of two to four carbon atoms, and X is carboxy.

The following examples are offered by way of illustration and not by way of limitation.

EXPERIMENTAL

All of the temperatures not otherwise indicated are in centigrade. All parts and percents not otherwise indicated are by weight, except for mixtures of liquids, which are by volume. The following abbreviations are used:

PBS, N$_3$, Mg—phosphate buffered saline 0.10 mM PO$_4$, pH 7.0, 0.128 M NaCl, 5 mM sodium azide, 1 mM Mg as acetate;

DMF—N,N-dimethyl formamide;

NHS—N-hydroxy succinimide;

RSA—rabbit serum albumin (1 mg/ml);

DEAE—diethylaminoethyl;

RT—room temperature;

EDCI—ethyl dimethylaminopropyl carbodiimide;

ONPG—o-nitrophenylgalactoside.

EXAMPLE 1

Conjugation of β-galactosidase to sheep anti(human IgG) (sheep antiHIgG).

A. The β-galactosidase was prepared as follows. A 10 ml aliquot of β-galactosidase (Boehringer 150797, 8.5 mg/ml) was centrifuged for 10 min and the precipitate dissolved in 3 ml PBS, N$_3$Mg. To the mixture was then added 0.3 ml 100 mM dithioerythritol and the mixture incubated for 1 hr at room temperature, followed by chromatographing on a 2.6×75 cm Biogel A5M (200–400 mesh) column equilibrated with PBS, N$_3$, Mg, the total volume being 390 ml. The solution was eluted at 12 ml/hr and 80 drop fractions (5 ml) collected. Tubes 39–44 were pooled to a volume of 28.9 ml, having a concentration of 1.47 mg/ml. The enzyme was then assayed and found to have an activity of 477 u/mg of protein.

B. Sheep antiHIgG serum was precipitated with an equal volume of saturated ammonium sulfate and the precipitate dissolved in a final volume after dialysis of 154 ml of 0.01 M phosphate, pH 6.5. The IgG fraction was further purified by chromatography on a 5×60 cm column (1178 ml) of DEAE-Sephadex A50 equilibrated with the same phosphate solvent. Based on electrophoretic patterns and yield of protein, it was established that all of the IgG had not been eluted so the column was further eluted with buffer to which 0.15 M NaCl had been added at a rate of about 150 ml/hr, collecting 25 ml fractions. Fractions 133-142 were pooled for a volume of 250 ml and based on absorption at 280 nm, the concentration was found to be 9.96 mg/ml. The protein was assayed for the desired antibody, which is found to be present at a concentration of 1.78 mg/ml for a specific activity of the antibody based on total protein of about 18%. The protein was precipitated by an equal volume of ammonium sulfate and dissolved in PBS, $N_3$, Mg to give a solution containing 35 mg/ml protein.

C. To 1.8 ml of a 35.3 mg/ml solution of the antiHIgG was added 60 μl (10 mg/ml DMF) of m-maleimidobenzoic acid NHS ester and the mixture allowed to stand at room temperature for 30 min, followed by the addition of 0.18 ml of 1 M sodium acetate, pH 5. The reaction mixture was then dialyzed 2×500 ml (degassed) 20 mM sodium acetate, pH 5, 0.15 M NaCl for 1 hr at room temperature. To a solution of 5 ml of β-galactosidase (1.47 mg/ml) was added 0.2 ml of 0.5 M phosphate, pH 7, followed by 2 ml of the above reaction product at a concentration of 31.1 mg/ml and the mixture incubated at room temperature for 4 hrs. The reaction was terminated by the addition of 0.2 ml of 10 mM cysteine-HCl and incubating for 0.5 hr to yield a final volume of 7.4 ml. The product was chromatographed on a Biogel A5M column (2.6×75 cm, 398 ml) equilibrated with PBS, $N_3$, Mg and eluted with the same solvent at 12 ml/hr collecting 5 ml fractions. Fractions 24 to 33 were collected to provide a volume of 50 ml with an optical density at 280 nm of 0.540 and a molar ratio of antibody to enzyme of about 5:1. The concentration of β-galactosidase was found to be 121 μg/ml, while the concentration of sheep IgG was found to be 213 μg/ml. Assaying for the enzyme employed a 10 μl fraction dissolved in 0.5 ml PBS, $N_3$, Mg, RSA combined with 0.1 ml 20 mM ONPG in 0.4 ml buffer and measuring the rate at 37° at 420 nm for the interval between 10 to 20 secs after addition of the substrate.

D. The above procedure was repeated as follows. To 1.8 μl of sheep antiserum to HIgG (35.3 mg protein/ml) was added 60 μl of a 32 mM solution of m-maleimidobenzoic acid NHS ester and the mixture stirred at RT for 30 min. After adding 0.18 ml 1.0 M NaOAc, pH 5.0, the solution was dialyzed against 2×500 μl (degassed) 20 mM NaOAc, pH 5.0, 0.15 M NaCl over 1 hr at RT. To 5 ml of β-galactosidase (1.47 mg/ml) was added 0.2 ml of 0.5 M $PO_4$, pH 7.0, followed by 2 ml of the above solution (31.1 μg/ml) and the mixture incubated at RT for 4 hrs. The reaction was terminated by the addition of 0.2 ml 10 mM cysteine HCl followed by incubating for 0.5 hr. The product was chromatographed on Biogel A5M (2.6×75 cm) equilibrated with PBS, $N_3$, Mg, eluting with the same solvent at a rate of 12 ml/hr collecting 5 ml fractions with fractions 24-33 pooled. The activity of the conjugate as compared to the activity of the enzyme with o-nitrophenyl galactoside (ONPG) as substrate was found to be 96%, while the comparative activity with ONPG bonded to DX 2000 (dextran 2 M mol.wt.) was 38.6%. The assays were performed at 37° C., reading at 420 nm employing an assay solution of 10 μl of the conjugate, 0.9 ml PBS, $N_3$, Mg, RSA and 0.1 ml of substrate (20 mM ONPG).

EXAMPLE 2

Succinylation of sheep anti(human IgG)

After dialyzing 5 ml of sheep anti(human IgG) (35.3 mg/ml) with 3×0.5 l 0.1 M $Na_2HPO_4$, at room temperature overnight, the resulting 5.3 ml (187.1 mg) was diluted with 4 ml of the $Na_2HPO_4$ solution and 250 μl of a 1 M solution of $^{14}$C-succinic anhydride was added with stirring. The pH was maintained above 7.5 by addition of 1 M sodium hydroxide, the total volume added being 400 μl. After 0.5 hr, 1 ml of a 1 M hydroxylamine-HCl adjusted to pH 8 with sodium hydroxide was added and the mixture incubated at room temperature for 30 min before dialyzing 5×0.5 l. PBS, $N_3$, Mg at room temperature overnight. The final volume was 10.7 ml having a concentration of 17.4 mg/ml.

EXAMPLE 3

Fluorescein labeling of sheep anti(HIgG)

Sheep antiserum to human IgG (5 ml, 176.5 mg sheep IgG) was dialyzed 3×500 ml 0.1 M $Na_2CO_3$ buffer, pH 9.0, at RT overnight. Dialysis buffer (3.75 ml) was added to give a total volume of 8.65 ml. To 2.7 ml of the protein solution (54 mg, 0.33μ mole) was added 25 μl of a 50 mg/ml fluorescein isothiocyanate DMF solution (9.2 fluorescein/protein mole ratio) and the mixture stirred at RT in the dark. The product was gel filtered on Sephadex G25M with PBS pH 6.8 $N_3$, Mg, to yield 7.3 ml of labeled protein having an F/P ratio of 6.8.

EXAMPLE 4

Dextran 40-ONPG

A. Methyl 3-Hydroxy-4-Nitrobenzoate (II).

3-Hydroxy-4-nitrobenzoic acid (I) (100.3 g, 95% pure, 0.53 mole) was added to methanol (1250 ml) to which had been added acetyl chloride (25 ml). The solid dissolved over a period of two days. After six days, the solution was filtered to remove undissolved impurities. The crude ester was obtained by evaporation of the solution. Several crops of crystals were taken, the last from a 50 ml volume. The combined crops were recrystallized from methanol (150 ml). Two crops of the ester (II) as yellow-brown crystals, m.p. 89°–91°, (98.7 g, 0.50 mole) were obtained.

B. Methyl 3-(2,3.4.6-Tetraacetyl-β-Galactosyloxy)-4-Nitrobenzoate (IV)

Acetobromogalactose (III) (100.1 g, 95% pure, 0.23 mole) and methyl 3-hydroxy-4-nitrobenzoate (II) (45.5 g, 0.23 mole) were dissolved in acetonitrile (600 ml). Silver oxide (30 g, 0.26 equiv.) was added to the stirred solution. The black solid gradually turned gray. After ten minutes, an additional portion of silver oxide (20 g, 0.17 equiv.) was added. Stirring was continued for an additional twenty minutes. The reaction mixture was filtered through a Celite pad to remove the silver salts. The filtrate was evaporated to give a crude brown crystalline mass (115 g). This material was recrystallized from ethanol (400 ml). Two crops of off-white crystals, m.p. 150°–152° (99.6 g, 0.19 mole, 83% yield) were obtained.

C. Methyl 3-β-Galactosyloxy-4-Nitrobenzoate (V)

The tetraacetate IV (119 g, 0.226 mole) was added to methanol (1000 ml). The mixture was heated at 60° until the solid dissolved. Triethylamine (25 ml) was then added, and the solution was heated at 60° for an additional two hours. The crude solid product was obtained in several crops by evaporation of the solution, the final crop being taken from a 20 ml volume. The crude material was used in the next reaction without further purification.

D. 3-β-Galactosyloxy-4-Nitrobenzoic Acid (VI)

The crude ester V (prepared from 119 g of tetraacetate IV in the preceding reaction) was added with stirring to 1 N NaOH (1500 ml). After 15 min, the ester had dissolved and hydrolyzed. The solution was neutralized with concentrated HCl to give a cloudy orange solution, pH 7.5. The solution was clarified by filtration, then acidified with 1 N HCl (250 ml) to give a light yellow solution, pH 3–3.5. The acid VI precipitated and was collected by filtration. It was washed with water (20 ml), giving silky white needles (34.7 g). The aqueous mother liquors were concentrated to an 800 ml volume and acidified to pH 2. An additional amount of the crude acid was obtained which was recrystallized from methanol (150 ml) to give needles (7.7 g). The total yield of purified acid VI was 42.4 g (123 mmoles), m.p. 172°–174°.

E. N-Hydroxysuccinimide Ester of 3-β-Galactosyloxy-4-Nitrobenzoic Acid (VII)

3-β-Galactosyloxy-4-nitrobenzoic Acid (55.2 g, 0.160 mole), N-hydroxysuccinimide (20 g, 0.174 mole), and EDCI (35 g, 0.183 mole) were dissolved in DMF (200 ml). After two hours, the reaction was complete by TLC-(10–20% MeOH/CHCl$_3$), and showed some minor impurities in addition to the desired compound VII. The solution was used without further treatment.

F. Carboxymethylated Dextran T40

Dextran T40 (~40,000 mw, 101 g) was dissolved in 1.25 M aqueous sodium chloroacetate (500 ml). A 2.5 M aqueous solution of sodium hydroxide (500 ml) was added. The solution was heated at 80°–85° for 3 hr.

The reaction mixture was allowed to cool. Ethanol (1 l) was added slowly to the stirred reaction mixture. The dextran began to precipitate after 350 ml had been added. Additional ethanol (2 l) was added to ensure complete precipitation.

The precipitate separated as a gum. The supernatant was decanted easily. The dextran was purified by three additional precipitations. These were carried out in the following manner. The gum was dissolved in water (750 ml). Ethanol (3 l) was then added slowly until a permanent cloudiness appeared in the solution, then more rapidly. The gummy precipitate of the dextran was then allowed to settle out overnight. The resultant product had about 20% of the glucose units carboxymethylated.

G. Amino-Dextran T40 (IX)

Carboxymethylated dextran T40 (as a gum, prepared from 100 g dextran T40) was dissolved in water (250 ml). A solution of N,N'-bis-(3-aminopropyl)piperazine (400 g, 2.00 mole) in hydrochloric acid (680 g of 8.52 mmole/g, 5.80 mole) was added. To the resulting solution was added EDCI (201 g, 1.05 mole) in water (250 ml). The reaction was stored at room temperature for 22 hrs. At the end of this period, ethanol (3 l) was added. The dextran began to precipitate after 1.5 l had been added. The precipitate was allowed to settle out overnight.

The aminodextran was purified by two additional precipitations. These were carried out as previously described. The final precipitation gave a milky suspension, which coagulated and settled out upon addition of a solution of lithium bromide (25 g) in ethanol (250 ml). The resulting gum was diluted to 1 l and found to be 140 mM in amino groups.

H. ONPG-dextran T40

A solution of the aminodextran IX (1 l of 104 mM, 104 mmole) was treated with K$_2$HPO$_4$ (89 g, 0.5 mole) to give a solution buffered at pH 8—8.1. A DMF solution of the NHS ester VII (prepared as described above from acid VI, 160 mmole) was added slowly. The resulting solution was stored at room temperature for 24 hr. The dextran was precipitated by the addition of ethanol (3 l). Precipitation began after addition of 350 ml of the ethanol. The precipitate was allowed to settle out overnight.

The dextran was purified by two additional precipitations in the manner already described. The final gum was dissolved in water (1 l). The solution was clarified by filtration first through a medium-porosity glass frit, and then through a 0.8μ Millipore filter.

The resulting solution was diluted to 2 l. A sample was diluted 1:121 and had A$_{320}$=1.15. Based on E$_{320}$=2700, the ONPG-group concentration was 52 mM.

The solution was preserved by addition of NaN$_3$ (0.65 g). Approximately half of the material was lyophilized. The residue reconstituted satisfactorily.

In order to demonstrate the subject invention, the following assays were carried out. In the first assay, the buffer was PBS, N$_3$, Mg, RSA and the solutions employed were the enzyme solution (Ex 1C) at 10 μg/ml in buffer, human IgG at 0.2 mg/ml and succinylated antibody at 17.4 mg/ml, the average number of succinic groups being 48 per molecule of protein. The substrate was an o-nitrophenylgalactosidyl ether bonded to dextran, (40,000 molecular weight) by a di(3-aminopropyl)-piperazine spacer, wherein the dextran was previously modified with sodium chloroacetate. The substrate was employed at 4 mM ONPG in PBS, N$_3$, Mg.

The protocol involved combining 0.05 ml of the enzyme-antibody conjugate and 0.10 ml of buffer with 0.05 ml of the appropriate concentration of human IgG and 0.10 ml of buffer and incubating the mixture for 3 hrs at room temperature. To the mixture was then added 0.1 ml of the succinylated antibody and 0.25 ml of buffer followed immediately (15 secs) by the addition of 0.10 ml of the substrate solution plus 0.25 ml of buffer. Measurements were made at 10 and 40 secs after the addition of substrate, the measurements being carried out at 37° C. and readings made at 420 nm. The following table indicates the results with a variety of HIgG dilutions and succinylated antibody dilutions, where the succinylated antibody dilution is one volume of the antibody solution to a final volume in buffer as indicated.

TABLE 3

| Ex. | HIgG dilution | Succinylated Ab dilution Rates (min⁻¹) | | | |
|---|---|---|---|---|---|
| | | 80 | 40 | 20 | 10 |
| 1 | ∞ | .264,.268 | .260,.266 | .276,.272 | .286,.290 |
| 2 | 2048 | .280 | .292 | .308 | .326 |
| 3 | 512 | .304 | .326 | .362 | .406 |
| 4 | 128 | .356 | .404 | .462 | .514 |
| 5 | 32 | .382 | .442 | .506 | .552 |
| 6 | 8 | .366 | .454 | .542 | .610 |

It is evident from the above table, that with increasing concentrations of the succinylated antibody, one obtains substantial enhancement of the observed rate of hydrolysis at a given concentration of the human IgG and that the change in the rate follows the change in concentration of the human IgG, increasing concentrations of human IgG providing for increasing rates.

In the next assay, the charged member employed fluorescein as the source of the negative charge. The assay was performed by combining 50 μl of the enzyme conjugate (Ex 1D) with 50 μl of HIgG in 0.2 ml buffer(PBS, $N_3$, Mg, RSA) and incubating the mixture for 1 hr at RT. To the mixture was then added 100 μl of the fluorescein labeled anti(HIgG) and 0.25 μl buffer, the mixture incubated for 15 sec at RT and 100 μl of 4 mM ONPG conjugated dextran (40,000 mw) in PBS, $N_3$ Mg+0.25 μl buffer and readings taken at 37°, at 420 nm with the reading taken at 10 sec after addition of substrate subtracted from the reading taken at 40 sec. The following table indicates the results.

TABLE 4

| HIgG dilution (0.2μg/ml) | Rate (min⁻¹) |
|---|---|
| ∞ | 0.398 |
| 4096 | 0.418 |
| 1024 | 0.448 |
| 256 | 0.502 |
| 64 | 0.582 |
| 16 | 0.624 |
| 4 | 0.726 |
| 1 | 0.828 |

As evidenced by the above results a two-fold enhancement in the rate is observed over the employed concentration range. The charged fluorescein carrying two negative charges is able to modulate the rate, enhancing the observed turnover rate of β-galactosidase when brought into proximity to the enzyme by the binding to the antigen HIgG.

In the next two assays, antienzyme was used as an inhibitor of enzyme which remains unbound to antigen. A mixture was prepared of 1.5 ml of the enzyme-antibody conjugate described previously and 1.5 ml of the succinylated antibody diluted 1:16. To 0.05 ml of the appropriate human IgG solution was added 0.10 ml of the above mixture and either (1) 0.05 ml antienzyme added within a few minutes or (2) the mixture incubated followed by the addition of 0.05 ml of the antienzyme. In each case, the mixtures were then incubated for 1 hr at room temperature followed by the addition of 0.10 ml of 4 mM ONPG-dextran 40 conjugate plus 0.7 ml buffer, and readings taken at 10 and 40 secs at 37° C., reading at 420 nm. The following indicates the observed results. The antienzyme was employed in buffer at a concentration sufficient to substantially saturate all of the enzyme binding sites.

TABLE 5

| Ex | HIgG dilution | Protocol | Rate (mm⁻¹) | % of rate at O HIgG |
|---|---|---|---|---|
| 1 | ∞ | 1 | 0.80,0.82 | 100 |
| 2 | 1024 | | 0.80 | 99 |
| 3 | 512 | | 0.78 | 96 |
| 4 | 256 | | 0.82 | 101 |
| 5 | 128 | | 0.86 | 106 |
| 6 | 64 | | 0.102 | 126 |
| 7 | 32 | | 0.122 | 151 |
| 8 | 16 | | 0.158 | 195 |
| 9 | 8 | | 0.208 | 257 |
| 10 | 4 | | 0.240 | 296 |
| 11 | 2 | | 0.206 | 254 |
| 12 | ∞ | 2 | 0.76 | 94 |
| 13 | 1024 | | 0.80 | 99 |
| 14 | 512 | | 0.74 | 91 |
| 15 | 256 | | 0.82 | 101 |
| 16 | 128 | | 0.96 | 119 |
| 17 | 64 | | 0.104 | 128 |
| 18 | 32 | | 0.130 | 160 |
| 19 | 16 | | 0.176 | 217 |
| 20 | 8 | | 0.222 | 274 |
| 21 | 4 | | 0.268 | 331 |
| 22 | 2 | | 0.220 | 272 |

It is evident from the above results, that over a broad range of changes in concentration of human IgG, there is a substantial change in the observed rate as determined over a very short period of time, namely 30 sec. Thus, after allowing for the interaction between the antibodies and the antigen, one can rapidly determine the antigen, human IgG, by a simple rapid spectrophotometric technique.

Furthermore, one can enhance the accuracy of the assay by substantially eliminating the background from enzyme conjugate which is not involved with binding to antigen. In this way, the observed results are less sensitive to non-specific effects and variations in results due to enzyme conjugated to other than the homologous antibody of the analyte.

The subject invention provides a technique whereby impure antibody can be labeled and used in a sensitive assay for the determination of extremely small amounts of analyte. The method involves bonding a plurality of antibodies together, so as to provide that there is a major proportion of the label associated with the antibody to the ligand of interest. The signal obtained from a signal label in proximity to the charged member is substantially different from the signal obtained from a signal label uninfluenced by the charged member. Thus, there is substantial differentiation between label bonded, directly or indirectly, to antiligand of interest and label bonded to other proteins present in antisera.

In accordance with the subject invention, a simple sensitive rapid assay is provided for determinating a wide variety of analytes. The technique permits a wide range of different labels to be employed, where the label can be influenced by the presence of an electric field in an aqueous medium. The field is supplied by modifying a member of a specific binding pair with a plurality of substituents which are ionized under the conditions of the assay medium to provide for a relatively concentrated charge environment.

While the subject method has been demonstrated employing as reagents antibodies directed to the analyte of interest, it is evident that one could employ antibodies to the antibodies as universal reagents and modify the antiantibody for providing charges or labels. In this way, one can greatly amplify or proliferate the number of labels and charges brought together by an analyte.

This technique can be employed most effectively when relatively pure anti-antibody is available.

Although the foregoing invention has been described in some detail by way of illustration and example for purposes of clarity of understanding, it will be obvious that certain changes and modifications may be practiced within the scope of the appended claims.

What is claimed is:

1. A method for determining the presence of an analyte in a sample suspected of containing said analyte, said analyte being a member of a specific binding pair consisting of ligand and antiligand, wherein a detectible signal is obtained related to the amount of analyte by employing a signal producing system comprising an enzyme labeled specific binding member and a polyionic charged specific binding member having sufficient charge to attract an oppositely charged macromolecular substrate or cofactor, where the detectible signal level is related to the average proximity of said charged member to said enzyme labeled member, said method comprising:

combining in an aqueous assay medium;
(1) said sample;
(2) said charged specific binding member;
(3) said enzyme labeled specific binding member;
(4) substrates and cofactors for said enzyme wherein at least one substrate or cofactor for said enzyme is a charged macromolecular of opposite charge from said polyionic charged member, wherein at least one of (1), (2) and (3) is ligand and at least one of the remaining of (1), (2) and (3) is antiliand, so that a complex may be formed between said charged specific binding member and said enzyme labeled specific binding member; and determining the detectible signal produced by said enzyme as compared to the signal produced in an assay medium having a known amount of analyte.

2. A method according to claim 1, wherein said substrate is said charged macromolecule having enzymatically hydrolyzable bonds.

3. A method according to claim 2, wherein said charged macromolecular substrate has a positive charge.

4. A method according to any of claims 1 to 3, wherein said aqueous assay medium is at a pH in the range of about 5 to 10.

5. A method according to any of claims 1 to 3, wherein said charged member has a plurality of carboxy groups.

6. A method according to any of claims 1 to 3, wherein said charged member has a plurality of phenolic groups.

7. A composition useful for the immunoassay of claim 1 comprising, a macromolecular charged substrate or coenzyme and modified members of a specific binding pair consisting of ligand and antiligand, wherein the modified members are an enzyme labeled member and a charged member substituted with a plurality of functionalities which under the conditions of the assay are sufficiently charged opposite to said charged macromolecular substrate or cofactor to attract said charged macromolecular substrate or cofactor, the relative amounts of said charged member and said enzyme-labeled member substantially optimize the response of the detectible signal level to variations in analyte concentration.

8. An assay composition according to claim 7, wherein said charged member is polycarboxyl substituted antiligand and said signal labeled member is $\beta$-galactosidase substituted antiligand.

9. An assay composition according to claim 7, wherein said macromolecular charged substrate is a positively charged substrate for said $\beta$-galactosidase having a plurality of o-nitrophenylgalactoside groups.

10. An assay composition according to claim 7, wherein said charged member is a polyphenolic substituted antiligand and said signal labeled member is $\beta$-galactosidase labeled antiligand.

11. An assay composition according to claim 10, wherein said charged macromolecular substrate is a positively charged substrate for said $\beta$-galactosidase having a plurality of o-nitrophenylgalactoside groups.

12. A method for determining the presence of an antigenic protein in a sample suspected of containing said antigenic protein, said antigenic protein being a member of a specific binding pair consisting of said antigenic protein and antibody to said antigenic protein, wherein a detectible signal is obtained related to the amount of antigenic protein by employing a signal producing system including a labeled member, said labeled member being enzyme conjugated to said antibody, and a polyionic charged member, wherein said charged member is said antibody substituted with a plurality of carboxyl groups, where the detectible signal level is related to the average proximity of said charged member to said labeled member, said method comprising:

combining in an aqueous assay medium:
(1) said sample;
(2) said charged member;
(3) said signal labeled member;
(4) said enzyme substrates and co-factors; and determining the detectible signal produced by said signal producing system as compared to the signal produced in an assay medium having a known amount of said protein antigen.

13. A method according to claim 12, wherein said enzyme is $\beta$-galactosidase and said substrate is a positively charged macromolecular substrate having a plurality of o-nitrophenylgalactoside groups.

14. A method for determining the presence of an antigenic protein in a sample suspected of containing said antigenic protein, said antigenic protein being a member of a specific binding pair consisting of said antigenic protein and antibody to said antigenic protein, wherein a detectible signal is obtained related to the amount of antigenic protein by employing a signal producing system including a labeled member, said labeled member being enzyme conjugated to said antibody, and a polyionic charged member, wherein said charged member is said antibody substituted with a plurality of phenolic groups, where the detectible signal level is related to the average proximity of said charged member to said labeled member, said method comprising:

combining in an aqueous assay medium:
(1) said sample;
(2) said charged member;
(3) said signal labeled member;
(4) said enzyme substrates and co-factors; and determining the detectible signal produced by said signal producing system as compared to the signal produced in an assay medium having a known amount of said protein antigen.

15. A method according to claim 14, wherein said enzyme is $\beta$-galactosidase and said substrate is a positively charged macromolecular substrate having a plurality of o-nitrophenylgalactoside groups.

* * * * *